US008628671B2

(12) United States Patent
Eagle et al.

(10) Patent No.: US 8,628,671 B2
(45) Date of Patent: Jan. 14, 2014

(54) METHOD FOR PRE-FILTERING BLOOD IN A BLOOD COLLECTION AND PROCESSING SYSTEM

(75) Inventors: Jonathan Eagle, Weston, MA (US); Donald J. Schwarz, Bridgewater, MA (US); Seth Kasper, Cambridge, MA (US); Steve Mastroyin, Pawtucket, RI (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 13/418,509

(22) Filed: Mar. 13, 2012

(65) Prior Publication Data

US 2012/0168377 A1 Jul. 5, 2012

Related U.S. Application Data

(63) Continuation of application No. 12/564,514, filed on Sep. 22, 2009, now Pat. No. 8,157,103.

(51) Int. Cl.
*B01D 37/00* (2006.01)
*B01D 24/34* (2006.01)
*B01D 35/30* (2006.01)
*B01D 35/14* (2006.01)
*B01D 33/333* (2006.01)

(52) U.S. Cl.
USPC ............. 210/780; 210/91; 210/97; 210/104; 210/232; 210/236; 210/248; 210/329; 210/359; 210/649; 210/650

(58) Field of Classification Search
USPC ............ 210/91, 97, 104, 232, 236, 248, 329, 210/359, 649, 650, 780
See application file for complete search history.

(56) References Cited

U.S. PATENT DOCUMENTS

| 3,768,653 | A | | 10/1973 | Brumfield ................. 210/188 |
|---|---|---|---|---|
| 4,033,345 | A | * | 7/1977 | Sorenson et al. .......... 604/6.09 |
| 4,054,523 | A | | 10/1977 | Ingenito et al. ............. 210/188 |
| 4,115,277 | A | | 9/1978 | Swank ....................... 210/436 |
| 4,243,531 | A | | 1/1981 | Crockett et al. ............ 210/188 |
| 4,531,954 | A | | 7/1985 | Klein ......................... 55/159 |
| 4,561,868 | A | | 12/1985 | von Reis et al. ............ 55/319 |

(Continued)

FOREIGN PATENT DOCUMENTS

| EP | 0 573 117 A1 | 12/1993 |
|---|---|---|
| EP | 0573117 A1 * | 12/1993 |
| EP | 0 771 570 | 5/1997 |
| WO | 00/38756 | 7/2000 |

OTHER PUBLICATIONS

European Patent Office, International Search Report and Written Opinion of the International Searching Authority—Application No. PCT/US2010/048452, dated Nov. 25, 2010 (13 pages).

*Primary Examiner* — John Kim
(74) *Attorney, Agent, or Firm* — Sunstein Kann Murphy & Timbers LLP (57) ABSTRACT

A reservoir for use with a blood collection system includes a housing, a pre-filter, and a spring mechanism. The housing defines a cavity and has an inlet for receiving fluid from a source. The pre-filter is located within the cavity, removes particulates contained within the fluid, and allows the fluid to pass through the pre-filter. The spring mechanism is connected to the pre-filter and allows the pre-filter to travel within the cavity as the pre-filter collects particulates.

10 Claims, 7 Drawing Sheets

(56) References Cited

U.S. PATENT DOCUMENTS

| | | | | |
|---|---|---|---|---|
| 4,673,423 A | | 6/1987 | Yumlu | 55/319 |
| 4,681,677 A | * | 7/1987 | Kuh et al. | 210/88 |
| 4,704,203 A | | 11/1987 | Reed | 210/188 |
| 4,743,371 A | | 5/1988 | Servas et al. | 210/188 |
| 4,758,337 A | | 7/1988 | Köhn et al. | 210/94 |
| 4,898,572 A | | 2/1990 | Surugue nee Lasnier et al. | 604/4 |
| 4,954,251 A | | 9/1990 | Barnes et al. | 210/806 |
| 5,015,388 A | | 5/1991 | Pusineri et al. | 210/641 |
| 5,055,198 A | | 10/1991 | Shettigar | 210/650 |
| 5,133,703 A | | 7/1992 | Boehringer et al. | 604/317 |
| 5,135,645 A | * | 8/1992 | Sklenak et al. | 210/97 |
| 5,183,569 A | | 2/1993 | Kyriacou | 210/636 |
| 5,215,519 A | | 6/1993 | Shettigar | 604/4 |
| 5,223,154 A | | 6/1993 | MacPherson, Jr. et al. | 210/790 |
| 5,411,705 A | | 5/1995 | Thor et al. | 422/45 |
| 5,423,738 A | * | 6/1995 | Robinson et al. | 604/6.01 |
| 5,674,173 A | | 10/1997 | Hlavinka et al. | 494/17 |
| 5,725,777 A | * | 3/1998 | Taylor | 210/650 |
| 5,770,073 A | | 6/1998 | Bach et al. | 210/472 |
| 5,800,721 A | | 9/1998 | McBride | 210/506 |
| 5,879,624 A | | 3/1999 | Boehringer et al. | 422/44 |
| 6,251,291 B1 | | 6/2001 | Lamphere et al. | 210/767 |
| 8,157,103 B2 | | 4/2012 | Eagle et al. | 210/359 |

\* cited by examiner

*FIG. 6*

METHOD FOR PRE-FILTERING BLOOD IN A BLOOD COLLECTION AND PROCESSING SYSTEM

PRIORITY

This application is a continuation of U.S. patent application Ser. No. 12/564,514, entitled "A Reservoir For Use with A Blood Collection System," filed Sep. 22, 2009, now U.S. Pat. No. 8,157,103 and naming Jonathan Eagle, Donald J. Schwarz, Seth Kasper, and Steve Mastroyin as inventors, the disclosure of which is incorporated herein, in its entirety, by reference.

TECHNICAL FIELD

The present invention relates to methods and systems for receiving, storing, and filtering fluids during extracorporeal blood processing, and more particularly to pre-filtering blood entering blood processing equipment and storage devices.

BACKGROUND ART

It is well known that patients undergoing surgery lose blood both during and after surgery. To compensate for this blood loss, physicians and medical practitioners must replenish the volume of blood lost by the patient and may do so in variety of way. One such known method is to give the patient a blood transfusion with allogenic blood. However, allogenic blood is expensive and the transfusion puts the patient at risk for infection and complications.

To avoid the use of allogenic blood, physicians and medical practitioners often use blood salvage and processing systems. These blood salvage and processing systems allow the physician and/or medical practitioner to collect the patient's own blood, process (e.g., wash) the blood, and autotransfuse the patient with their own blood or blood components. Autotransfusions with the patient's own blood greatly reduce the risk of infection and complications to the patient.

As mentioned above, blood loss not only occurs during surgery, but also post-operative. Accordingly, physicians and medical practitioners often utilize a wound drain to drain the blood from the surgical site. This wound drain may, in turn, be connected to a blood salvage and processing system in order to salvage the blood lost postoperatively.

As one may expect, the blood and fluid removed via the wound drain may contain various particulates such as debris and blood clots. To prevent these particulates from entering the blood processing system and interfering with the system's performance, current systems use filters located between the wound and the blood processing system to remove the particulates.

The volume of particulates collected by the filters may be important information. For example, if the volume of collected particulates is exceptionally large, it may be an indication of postoperative complications. Additionally, in some instances, physicians and medical practitioners may use this information to determine if additional fluids (e.g., compensation fluid or allogenic blood) should be returned to the patient (e.g., in addition to their own blood). Currently, to determine the volume of particulates, physicians and medical practitioner simply do a visual estimation. This visual estimation is qualitative and inaccurate.

SUMMARY OF THE INVENTION

In a first embodiment of the invention there is provided a reservoir for use with a blood collection system. The reservoir may include a housing defining a cavity, a pre-filter located within the cavity, and a spring mechanism. The housing may have an inlet that is in fluid communication with the cavity and receives fluid from a source (e.g., a wound drain). The pre-filter may receive and pre-filter the fluid entering the housing from the inlet. For example, the pre-filter may remove particulates (e.g., debris and clots) out of the fluid. The pre-filtered fluid may pass through the pre-filter.

The spring mechanism allows the pre-filter to travel within the cavity as it collects particulates. Additionally, the reservoir may have a track within the cavity that extends along at least a portion of the housing's inner wall. The pre-filter may have a location arm extending into and moveable within this track. A sensor may detect the position of the location arm as the pre-filter travels within the cavity. The position of the arm and the distance traveled by the pre-filter may correspond to a weight and a volume of particulates collected within the pre-filter.

In accordance with some embodiments, the pre-filter may have a pre-filter housing that defines the structure of the pre-filter, and a pre-filter membrane (e.g., a mesh or a polyester screen) within the pre-filter housing. The pre-filter membrane pre-filters the fluid by preventing the particulates from passing through and allowing the fluid to pass through. The pre-filter may be conical in shape, which causes the particulates to be collected within the center of the pre-filter.

The reservoir housing may include at least one curved wall. For example, the reservoir housing may have a D-Shaped cross-section in a horizontal plane. Additional embodiments of the present invention may also include a filter located within the cavity. The filter may be located downstream of the pre-filter, and it may divide the cavity into a first portion and a second portion. The pre-filter may be located within the first portion. The second portion may collect filtered fluid passing through the filter, and may be in fluid communication with the reservoir outlet which, in turn, may be connected to a blood processing device. The filtered fluid may be extracted from the reservoir and into the blood processing device.

In accordance with further embodiments of the present invention, a pre-filter for use with a blood collection system may include a pre-filter housing and a pre-filter membrane. The pre-filter housing may define the structure of the pre-filter and may be located within a cavity of a reservoir, which, in turn, may be connected to the blood collection system. The pre-filter membrane (e.g., a mesh or polyester screen) may be contained within the pre-filter housing and may pre-filter fluid entering the reservoir from a source (e.g., a wound drain) by preventing particulates from passing and allowing the fluid to pass through the pre-filter membrane.

The pre-filter housing may also have a spring mechanism and a location arm. The spring mechanism may allow the pre-filter to travel within the cavity as the pre-filter collects particulates. The location arm may extend into and move within a track extending along at least a portion of the interior wall of the housing. A sensor (e.g., located within the blood processing device) may detect the position of the arm as the pre-filter travels within the cavity. The position of the location arm and the distance traveled by the location arm and/or the pre-filter may correspond to a weight and a volume of particulates collected within the pre-filter housing.

In accordance with additional embodiments, a method for pre-filtering blood in a blood collection and processing system includes connecting a reservoir to the blood collection and processing system, introducing blood into the reservoir through the inlet of the reservoir, and pre-filtering the blood introduced into the reservoir using a pre-filter. The pre-filter may be located within a cavity of the reservoir and may be in fluid communication with the inlet. The pre-filter may remove particulates out of the blood and allows the blood to pass through the pre-filter. The pre-filter may also have a spring mechanism that allows the pre-filter to travel within the cavity as the pre-filter collects particulates.

The pre-filter may also have a location arm and the method may also include detecting the distance traveled by the pre-filter within the cavity by sensing the position of the location arm. The location arm may extend into and move within a track extending along an inner wall of the reservoir.

In accordance with further embodiments, the method may also include determining the volume of particulates collected within the pre-filter. The volume of particulates collected within the pre-filter may be based, at least in part, upon the distance traveled by the pre-filter within the cavity. Additionally, the pre-filter may have a pre-filter housing and a pre-filter membrane. The pre-filter housing may define the structure of the pre-filter, and the pre-filter membrane may be contained within the pre-filter housing. The pre-filter membrane may prevent particulates from passing through the pre-filter and allow fluid to pass through the pre-filter. The pre-filter membrane may be, for example, a mesh or a polyester screen. The pre-filter housing may be conical in shape, which allows the particulates to be collected within the center of the pre-filter.

The reservoir may have a filter located within the cavity. Accordingly, the method may also include filtering the pre-filtered blood exiting the pre-filter. Moreover, the filter may divide the cavity into a first portion and a second portion. The pre-filter may be located within the first portion, and the filtered blood passing through the filter may be collected in the second portion. The method may also include extracting filtered blood from the second portion of the reservoir via an outlet, and introducing the extracted filtered blood into a blood processing device for further processing.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, a reservoir-and-filter system may be used in conjunction with blood processing systems and devices to allow physicians and medical practitioners to process a patient's own blood and return processed blood (or individual blood components) back to the patent. Additionally, some embodiments of the present invention allow physicians and/or medical practitioners to measure the amount of blood and/or fluid lost (e.g., the estimated blood loss volume) intra-operatively and/or post-operatively (e.g., from a wound drain).

Figure 1:
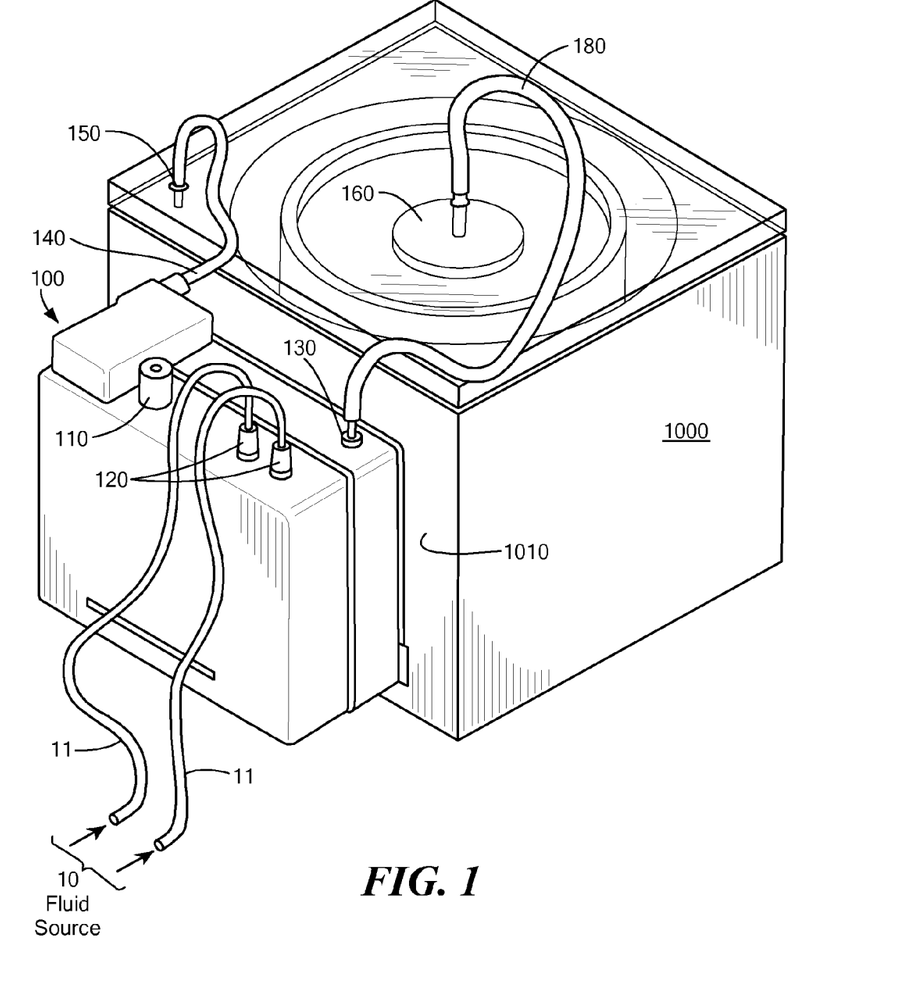
FIG. 1 is an isometric view of a blood processing device and reservoir, in accordance with some embodiments of the present invention.

FIG. 1 shows a reservoir 100 and a blood processing system 1000 in accordance with embodiments of the present invention. The reservoir 100 may be connected to a side 1010 of the blood processing device 1000. Tubing and various inlets and outlets may facilitate the transfer of fluids (e.g., blood and blood components) in and out of the reservoir 100 and blood processing device 1000. For example, unfiltered fluid obtained from a fluid source 10 (e.g., a wound drain, a blood storage container, an intra-operative surgical site, etc.) may be directed into the reservoir 100 through inlets 110, 120 (e.g., through tubes 11). It is important to note that the inlet used to introduce the fluid into the reservoir 100 may be dependent upon the application. For example, blood introduced intra-operatively may enter through inlets 120, whereas blood introduced post-operatively (e.g., from a wound drain) may enter through inlet 110. Moreover, because fluid introduced from a wound drain may contain sizeable particulates, inlet 110 may have a larger inner diameter to accommodate the particulates. Fluid may be removed from the reservoir 100 (e.g., for processing within blood processing device 1000) via the outlet 130. This outlet 130 may be fluidly connected to the blood processing device 1000 (and, in particular, a separation device 160) via fluid tube 180.

As mentioned above, fluids such a blood and blood products may enter and exit the reservoir 100. To that end, the reservoir 100 may be connected to a vacuum source 150 via vacuum line 140. The vacuum source 150 may be used to create vacuum and pressure differentials within the reservoir 100 and/or blood processing device 1000 to aid in the transfer of fluids in and out of the various components of the system.

As also mentioned above, the reservoir 100 and blood processing device 1000 may be used for a variety of applications (e.g., intra-operative, postoperative, etc.). For ease of understanding, illustrative embodiments described herein will be discussed in reference to a wound-drain application. However, it is important to note that the reservoir 100 and blood processing device 1000 described herein can be used for a variety of other applications including, but not limited to, intra-operative applications or other post-operative application.

In the wound drain application mentioned above, the fluid source 10 may be or may be in fluid communication with a post-operative surgical site where blood, clots, debris, and other fluids are present and/or generated. Prior to processing the fluid emanating from the wound site and/or returning some or all of the components back to the patient, it is important to remove debris and clots from the blood/fluid because such debris and clots may be problematic during processing and hazardous if returned to the patient. To that end, some embodiments of the present invention have various components within the reservoir 100 that pre-filter and filter the fluid entering through the inlet 110. These pre-filtration and filtration components are described in greater detail below.

Figure 2:
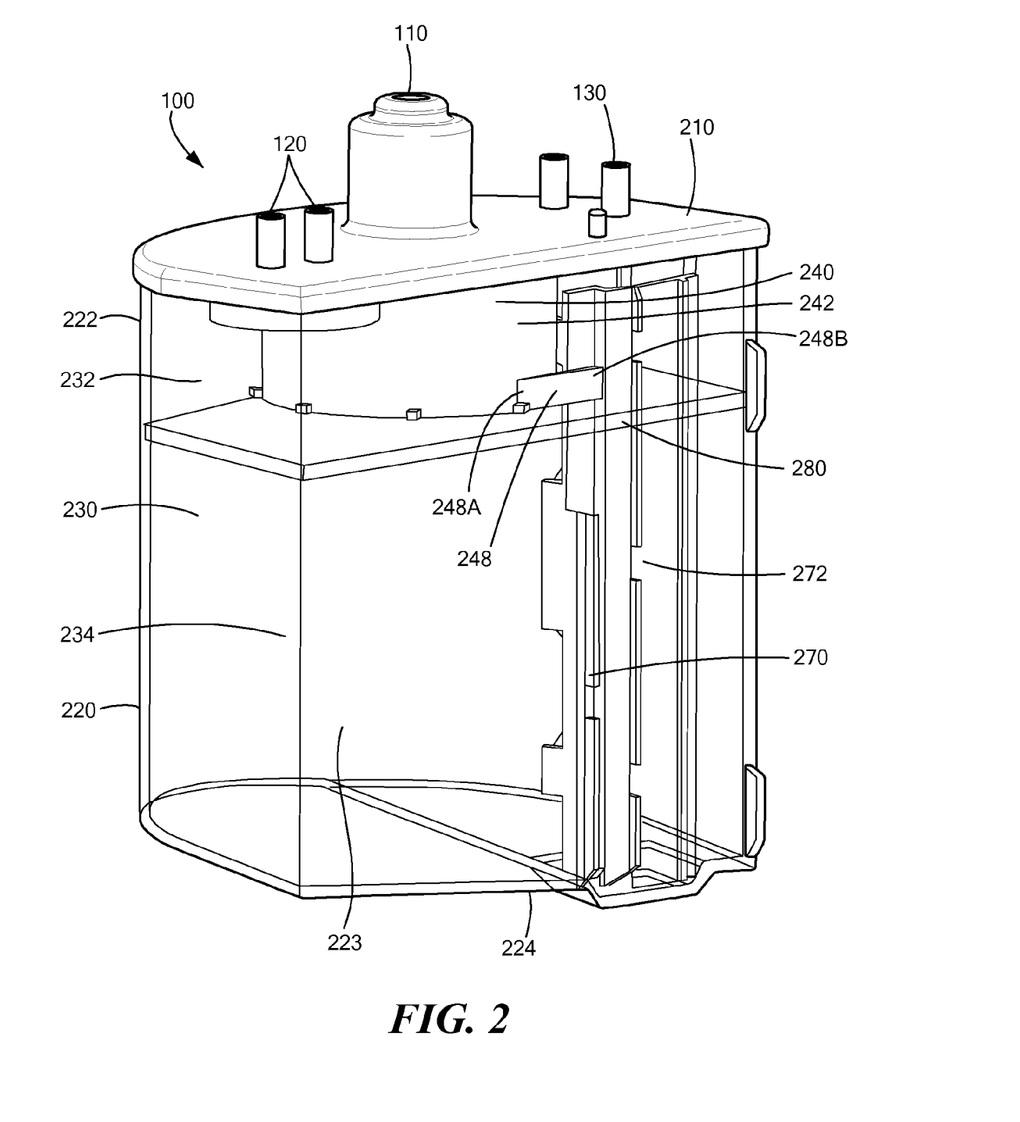
FIG. 2 schematically shows an isometric view of an alternative embodiment of a reservoir with the reservoir wall transparent to show the internal cavity of the reservoir, in accordance with some embodiments of the present invention.
Figure 3:
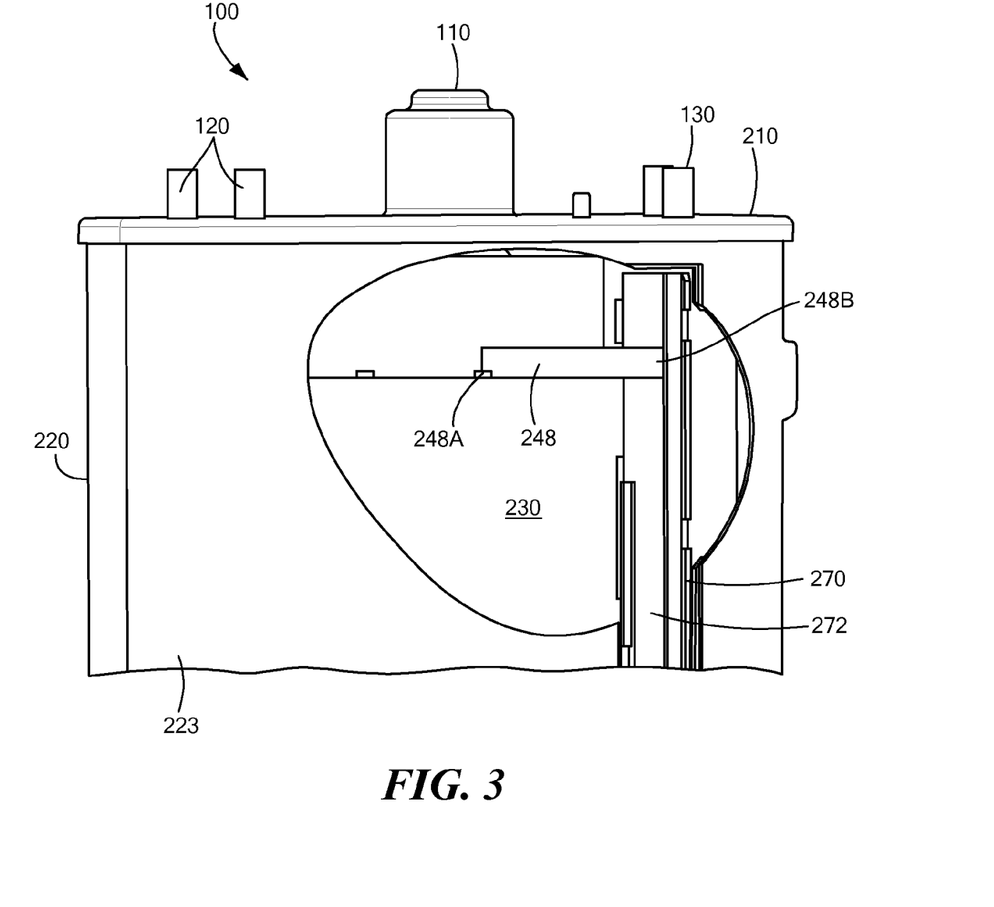
FIG. 3 schematically shows a side view of the reservoir with a portion of the reservoir wall removed to show the pre-filter, in accordance with some embodiments of the present invention.
Figure 4A:
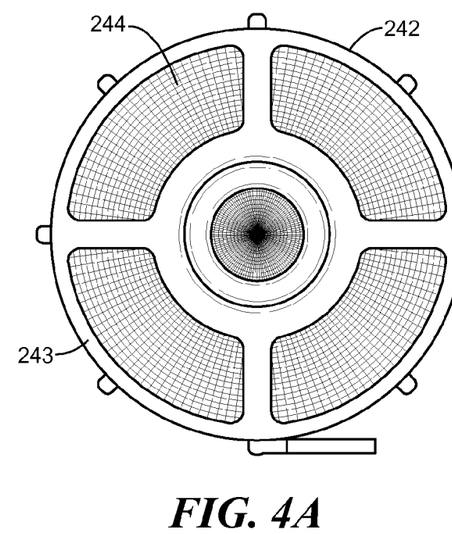
FIGS. 4A-4D schematically show various views of the pre-filter contained within the reservoir shown in FIGS. 2 and 3, in accordance with some embodiments of the present invention.
Figure 4B:
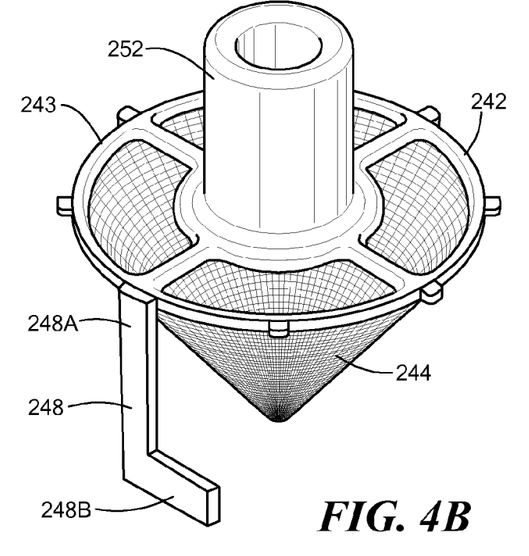
Figure 4C:
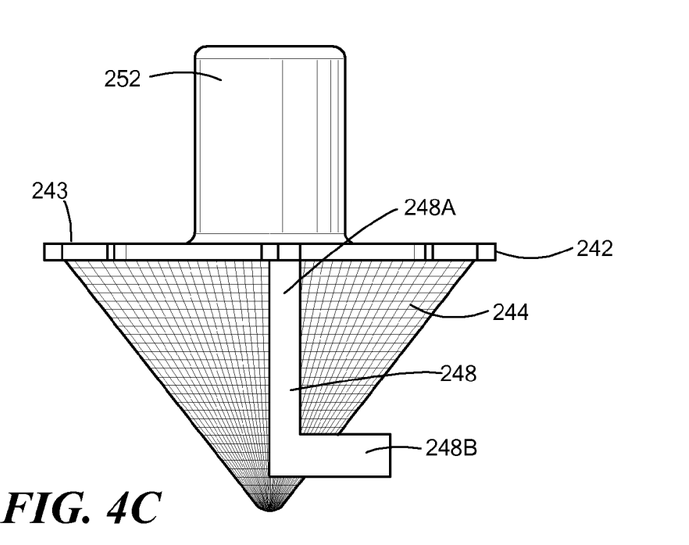
Figure 4D:
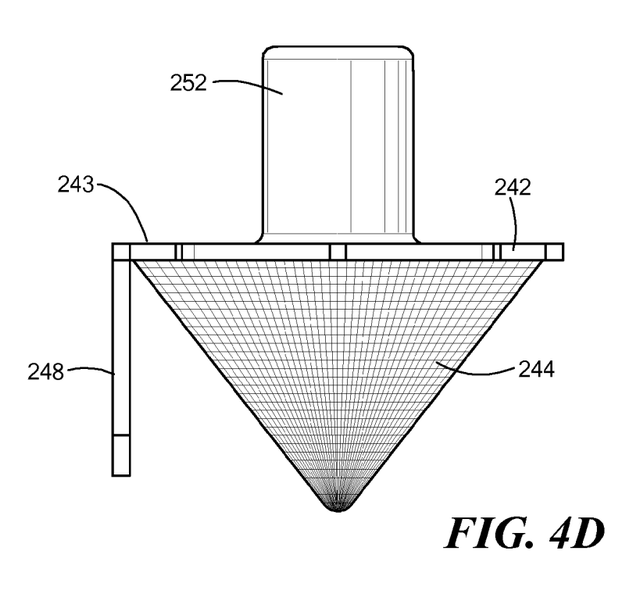

FIG. 2 shows an alternative embodiment of the reservoir 100 with a transparent wall in order to show the internal cavity of the reservoir 100. FIG. 3 shows a side view of the reservoir 100 with a section of the wall removed. As shown in FIGS. 2 and 3, the reservoir 100 may have a cover 210 and a housing 220 forming an internal cavity 230. The inlets 110/120 and the outlet 130 may be located within the cover 210. In order to increase structural strength and rigidity, the housing 220 may have at least one curved wall 222. For example, as shown in FIG. 2, the housing 220 may be D-shaped. If additional strength or rigidity is needed, the housing 220 may have ribs located on the walls.

As discussed in greater detail below, filtered blood is collected at the bottom of the reservoir 100. Accordingly, the outlet 130 may be fluidly connected to a dip-tube (not shown) extending from the outlet 130 to the bottom of the housing 220. In order to allow the maximum amount of blood/fluid to be extracted from the housing 220, the base 224 of the housing 220 may be angled toward the dip tube, ensuring that fluid within the housing 220 will flow towards and gather at the bottom of the dip-tube.

As mentioned above, illustrative embodiments of the present invention provide for pre-filtration and filtration of the fluid entering the reservoir 100. To that end, the reservoir 100 may have a pre-filter to remove debris, large particulates, and clots from the fluid as it enters the reservoir 100. For example, the reservoir 100 may have a pre-filter 240 located within the cavity 230 of the housing. The pre-filter 240 may be located just downstream of and in fluid communication with the inlet 110.

As shown in FIGS. 4A-4D, the pre-filter 240 may have a pre-filter housing 242 and a pre-filter membrane 244. The pre-filter housing 242 provides the structure and rigidity of the pre-filter 240. The pre-filter membrane 244 prevents debris, particulates, and clots from passing through the pre-filter 240, but allows the fluid to pass through the pre-filter 240 and enter the cavity 230. Although a variety of materials may be used for the pre-filter membrane 244, some embodiments of the present invention use a mesh or polymer screen. For example, the pre-filter membrane 244 may be a polymer screen with openings on the order of 500 to 800 microns.

As mentioned above, in many instances, it is helpful for physicians and medical practitioners to know an estimated blood loss volume. Accordingly, some embodiments of the present invention may have components that may be used by physicians and medical practitioners to estimate and determine blood loss volume. In particular, some embodiments of the reservoir 100 may include a spring mechanism 250 and a location arm 248. Each of these components and their role in estimating blood loss volume are described in greater detail below.

Figure 5:
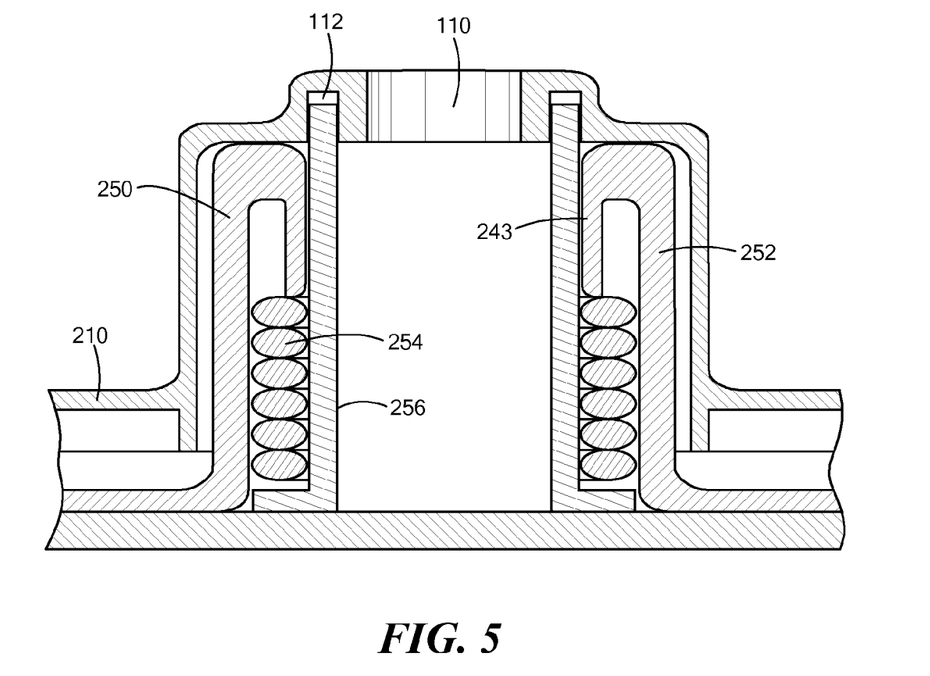
FIG. 5 schematically shows a cross-sectional view of the inlet of reservoir in accordance with some embodiments of the present invention.

As shown in FIGS. 2 and 3 and in greater detail in FIG. 5, the pre-filter 240 located within the reservoir cavity 230 may include a spring mechanism 250 that allows the pre-filter 240 to travel within the cavity 230 of the reservoir 100. For example, as the pre-filter 240 removes the debris and clots from the fluid entering the reservoir 100, the debris and clots begin to weigh down the pre-filter 240. The spring mechanism, in turn, will allow the pre-filter 240 to travel downward as the volume (and, thus the weight) of the collected debris/clots/particulates increases within the pre-filter 240.

As shown in FIG. 5, the spring mechanism 250 may have a spring housing 252 that extends into the inlet 110 located within the cover 210. Within the spring housing 252, the spring mechanism 250 may have a spring 254 that expands and compresses with the increasing and decreasing weight (e.g., created by the volume of debris/particulates/clots) within the pre-filter 240. This compression and expansion allows the pre-filter 240 to travel up and down within the reservoir 100. It is important to note that the distance that the pre-filter is allowed to travel within reservoir will be dependent upon the spring constant. Accordingly, springs having differing spring constants may be used depending on the application and/or expected volume of clots/debris to be collected. For example, if a large volume of clots is expected, a spring having a larger spring constant may be used to limit travel. Conversely, if only a small volume is expected, a spring with a lower spring constant may be used so that less weight is required to move the pre-filter 240.

In order to translate the weight of the pre-filter 240 to the spring (e.g., in order to compress the spring and allow the pre-filter 240 to move downward), the pre-filter housing 242 essentially encapsulates the spring 254 and may have a top portion 243 that rests on the top of the spring 254. Additionally, the spring mechanism 250 may also have a retainer sleeve 256 located radially inward from the spring 254. The retainer sleeve 256 secures the spring mechanism 250 and the pre-filter 240 to the cover 210. For example, the upper portion of the retainer sleeve 256 may be situated within an annular groove 112 located within the internal geometry of the cover 210 (e.g., within the inlet 110). In addition to securing the spring mechanism 250 and pre-filter 240 to the cover 210, the retainer sleeve 256 also prevents fluid and/or debris/particulates/clots from interfering with the operation of the spring 254.

The pre-filter 240 may also include a location arm 248 that moves up and down within the reservoir 100 with the pre-filter 240. A first end 248A of the location arm 248 may be attached to the pre-filter 240 and the opposing end 248B of the location arm 248 may be located within a track 270 located on and extending down a wall 223 of the reservoir housing 220. One side of the track 270 may be translucent to allow a sensor (e.g., a light or optical sensor) to detect the location of the location arm 248 and, thus, the distance traveled by the pre-filter 240. For example, the track 270 may be located within the flat wall 223 (see FIG. 2) adjacent to the blood processing device 1000, and the translucent side 272 of the track 270 may face the blood processing device 1000. In such embodiments, the blood processing device 1000 may have a sensor, such as an optical sensor or a camera that is capable of determining the location/position of location arm 248 through the translucent side 272 of the track 270. To help improve the accuracy and the ability of the sensor to detect the location arm 248, the arm 248 may have a mark (e.g., a colored dot or line) on the opposing end 248B located within the track 270.

It is important to note that, because the distance the pre-filter 240 travels within reservoir 100 is a function of the volume of debris/clots collected within the pre-filter 240 (e.g., the greater the volume of clots collected, the greater the distance traveled), an experienced physician or medical practitioner may use the information to quantitatively and accurately estimate the patient's blood loss volume. Alternatively, the blood processing system 1000 may have additional components (e.g., a microprocessor) that automatically calculate the estimated blood loss volume based on the pre-filter's travel distance and, perhaps, the spring constant of spring 254. The physician and/or medical practitioner may then use the estimated blood loss volume to adjust the amount of fluid (e.g., the patient's own blood, compensation fluid, or donor/allogenic blood) that is returned to the patient.

It should be noted that the pre-filter 240 can be a variety of shapes and/or sizes. For example, the pre-filter 240 may be conical (e.g., as shown in FIG. 4A-4D), frusto-conical, cylindrical, etc. However, preferred embodiments of the present invention utilize the conical shaped pre-filter 240 shown in FIGS. 4A-4D. In particular, as the pre-filter 240 collects the debris, particulates, and clots within the fluid entering the reservoir 100, the conical shape of the pre-filter 240 causes the collected material to gather at the bottom of the cone (e.g., starting at the point), minimizing the piling of debris/particulates/clots within the pre-filter 240. Additionally, because the mass of material will be centered within the pre-filter 240, the weight of the material will generate a more uniform, linear motion of the pre-filter 240 (e.g., as opposed to an off-center load that may cause the pre-filter to tip slightly and interfere with the movement of the pre-filter 240).

In embodiments having the conical pre-filter 240 described above, the location arm 248 may be L-shaped, as shown in FIGS. 4A-4D. The end (e.g., 248A) of vertical leg of the L-shaped location arm 248 may be attached to an annular ring 243 of the pre-filter housing 242 and extend perpendicularly downwards from the annular ring 243. The end (e.g., 248B) of the horizontal leg of the L-shaped location arm 248 may be located within track 270, as described above.

As mentioned above, the pre-filter 240 described above removes debris, particulates, and clots from fluid entering the reservoir 100 and allows the fluid to pass. In accordance with other embodiments of the present invention, this "pre-filtered" fluid may be further filtered after exiting the pre-filter 240. To that end, the reservoir 100 may also include a filter 280 located downstream of the pre-filter 240. The filter 280 may be oriented horizontally within the reservoir 100 such that it divides the cavity 230 into a first portion 232 (e.g., a pre-filtered portion) and a second portion 234 (e.g., a filtrate portion) (see FIG. 2). In other words, fluid that has passed through the pre-filter 240 will be within the pre-filtered portion 232 and fluid that has passed through filter 280 will be collected within the filtrate portion 234. The dip-tube described above may extend into the filtrate portion 234 so that only filtered fluid is removed from the reservoir 100 and sent to the blood processing device 1000.

Additionally, in embodiments having the horizontal filter 280, the track 270 may be divided into two portions. The top portion of the track 270 may located within the pre-filtered portion 232 of the cavity 230 and may be used to measure the distance traveled by the pre-filter 240, as described above. The bottom portion of the track 270 may be located within the filtrate portion 234 of the cavity 230, and may include a float (not shown). The float and the portion of the track 270 located within the filtrate portion 234 of the reservoir 100 may be used to determine the amount of filtered fluid contained within the reservoir 100. For example, the bottom of the track 270 may be open such that filtered fluid within the reservoir 100 will enter the bottom portion of the track 270 causing the float to rise with the fluid level. The optical sensor described above may then be used determine the fluid level within the reservoir 100 based on the height at which the float sits.

Figure 6:
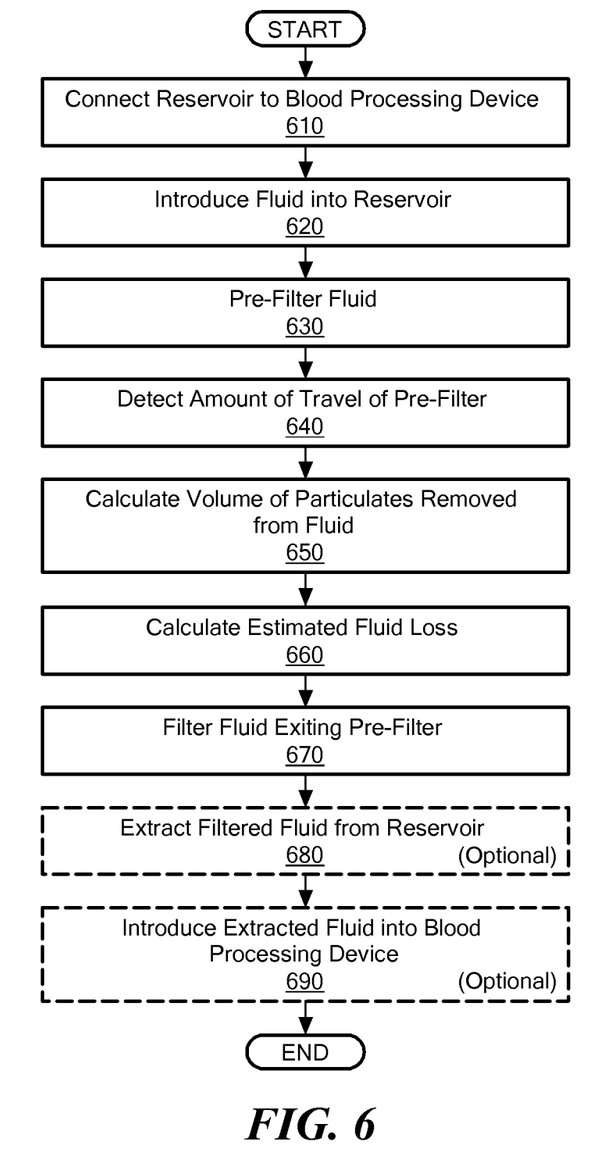
FIG. 6 is a flowchart showing a method of using the reservoir shown in FIG. 2 to pre-filter and filter blood, in accordance with some embodiments of the present invention.

FIG. 6 schematically shows a flowchart depicting a method of using the reservoir 100 and blood processing device 1000 described above. In particular, a physician or medical practitioner may connect the reservoir 100 to the blood processing device 1000 (Step 610). For example, the physician/medical practitioner may first connect the outlet 130 to the blood processing device 1000 using fluid tube 180, connect any required vacuum sources 150 or tubing 140, and orient the reservoir 100 such the flat wall 223 is adjacent the blood processing device and the optical sensor is capable of viewing the transparent side 272 of the track 270.

Once the reservoir 100 is connected, the physician/medical practitioner may then connect the fluid source 10 (e.g., the wound drain) to the inlet 110 and begin introducing the fluid into the reservoir 100 (Step 620). As the fluid enters the reservoir 100, the pre-filter 240 will remove the debris, clots, and particulates from the fluid (Step 630). As the debris, clots, and particulates begin to collect within the pre-filter 240, the weight of the pre-filter 240 will begin to compress the spring mechanism 250 and the pre-filter will travel downward within the cavity 230. The optical sensor may then detect the distance that the pre-filter 240 travels (e.g., by detecting the distance that the location arm 248 moves within the track 270) (Step 640). The blood processing system 1000, a different system, or the physician/medical practitioner may then calculate the volume of particulates removed from the fluid (Step 650). The blood processing system, different system, or the physician/medical practitioner may then, in turn, use the calculated volume to calculate the estimated fluid loss, as described above (Step 660).

After the incoming fluid has been pre-filtered, the fluid may then pass through the horizontal filter 280 (Step 670) and be collected in the filtrate portion 234 of the reservoir 100. Once within the filtrate portion 234 of the reservoir, the method may then, optionally, extract the filtered fluid from the reservoir 100 using the dip-tube and the outlet 130 (Step 680) and introduce the removed fluid into the blood processing device 1000 (Step 690) for further processing and/or return to the patient.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for pre-filtering blood in a blood collection and processing system comprising:
   connecting a reservoir to the blood collection and processing system, the reservoir having an inlet for receiving blood from a source and an outlet for removing filtered blood from the reservoir;
   introducing blood into the reservoir through the inlet; and
   pre-filtering the blood introduced into the reservoir using a pre-filter located within a cavity of the reservoir and in fluid communication with the inlet, the pre-filter removing particulates out of the blood and allowing the blood to pass through the pre-filter, the pre-filter having a spring mechanism that allows the pre-filter to travel within the cavity as the pre-filter collects particulates.

2. A method according to claim 1, further comprising:
   detecting a distance traveled by the pre-filter within the cavity by sensing a position of a location arm located on the pre-filter.

3. A method according to claim 2, wherein the location arm extends into and is moveable within a track extending along an inner wall of the reservoir.

4. A method according to claim 2 further comprising:
   determining the weight of particulates collected within the pre-filter, the volume of particulates collected within the pre-filter being based, at least in part, upon the distance traveled by the pre-filter within the cavity.

5. A method according to claim 1, wherein the pre-filter comprises:
   a pre-filter housing defining the structure of the pre-filter; and
   a pre-filter membrane contained within the pre-filter housing, the pre-filter membrane pre-filtering the fluid by preventing particulates from passing through the pre-filter membrane and allowing fluid to pass through the pre-filter membrane.

6. A method according to claim 5, wherein the pre-filter housing is conical such that particulates are collected within the center of the pre-filter.

7. A method according to claim 1, wherein the source of fluid is a wound drain and the inlet receives blood from the wound drain.

8. A method according to claim 1 further comprising:
filtering the pre-filtered blood exiting the pre-filter using a filter located within the reservoir cavity.

9. A method according to claim 8, wherein the filter divides the cavity into a first portion and a second portion, the pre-filter located within the first portion, the filtered blood passing through the filter into the second portion.

10. A method according to claim 9 further comprising:
extracting filtered blood from the second portion of the reservoir via an outlet in fluid communication with the second portion; and
introducing the extracted filtered blood into a blood processing device.

* * * * *